US00PP20790P2

(12) United States Plant Patent
Jandrew

(10) Patent No.: US PP20,790 P2
(45) Date of Patent: Feb. 23, 2010

(54) ***SCAVEOLA* PLANT NAMED 'BOMY WHIT'**
(50) Latin Name: *Scaveola aemula*
Varietal Denomination: Bomy Whit

(75) Inventor: Jason Jandrew, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/316,072

(22) Filed: Dec. 9, 2008

(51) Int. Cl.
*A01H 5/00* (2006.01)

(52) U.S. Cl. ..... Plt./363
(58) Field of Classification Search ..... Plt./363
See application file for complete search history.

*Primary Examiner*—Annette H Para
(74) *Attorney, Agent, or Firm*—S. Matthew Edwards

(57) ABSTRACT

A new *Scaveola* plant named 'Bomy Whit,' particularly distinguished by white flower color, early and abundant flowering response, medium green foliage, vigorous, initially semi-upright becoming decumbent to trailing habit with a well-branched plant habit.

1 Drawing Sheet

Latin name of the genus and species of the plant claimed: *Scaveola aemula.*

Varietal denomination: 'Bomy Whit'.

BACKGROUND OF THE NEW PLANT

The present invention comprises a new *Scaveola*, botanically known as *Scaveola aemula*, and hereinafter referred to by the variety name 'Bomy Whit.'

'Bomy Whit' is a product of a planned breeding program. The new cultivar 'Bomy Whit' has white flower color, early and abundant flowering response, medium green foliage, vigorous, initially semi-upright becoming decumbent to trailing habit with a well-branched plant habit.

'Bomy Whit' originated from a hybridization in a controlled breeding program in Gilroy, Calif., U.S.A. The female parent was an unpatented, proprietary hybrid seedling identified as '11-4' with white color. '11-4' has lighter foliage, is later to flower, and has fewer branches than 'Bomy Whit.'

The male parent of 'Bomy Whit' was 'Scawihatis' (U.S. Plant Pat. No. 15,003) with white color. 'Scawihatis' has smaller flowers, smaller and darker foliage, fewer branches, and thinner stems than 'Bomy Whit.'

'Bomy Whit' was selected as one flowering plant within the progeny of the stated cross in May 2006 in a controlled environment in Gilroy, Calif., U.S.A. The pollination took place in August 2005 and the seed sowing in January 2006.

The first act of asexual reproduction of 'Bomy Whit' was accomplished when vegetative cuttings were taken from the initial selection in the May 2006 in a controlled environment in Gilroy, Calif., U.S.A.

Horticultural examination of plants grown from cuttings of the plant initiated in May 2006 in Gilroy, Calif., U.S.A., and continuing thereafter, has demonstrated that the combination of characteristics as herein disclosed for 'Bomy Whit' are firmly fixed and are retained through successive generations of asexual reproduction.

'Bomy Whit' has not been observed under all possible environmental conditions. The phenotype may vary significantly with variations in environment such as temperature, light intensity and day length.

A Plant Breeder's Right for this cultivar was applied for in Canada on Dec. 24, 2007. 'Bomy Whit' has not been made publicly available more than one year prior to the filing of this application.

DESCRIPTION OF THE DRAWINGS

The accompanying photographic drawing shows typical flower and foliage characteristics of 'Bomy Whit' with colors being as true as possible with an illustration of this type. The photographic drawing shows 3 flowering potted plants of the new variety in a hanging basket and a close-up of the flowers. These plants were grown and photographed in Gilroy, Calif. U.S.A. in June 2008. These plants were approximately 5 months old.

DETAILED BOTANICAL DESCRIPTION

The measurements were taken on plants growing in Gilroy, Calif. U.S.A. in April 2008. The plants were growing in 4 inch pots in a greenhouse trial. These plants were about 3–4 months old.

Color Chart used: Royal Horticultural Society Colour Chart (R.H.S.) 2001.

BRIEF SUMMARY OF INVENTION

The following observations, measurements, and comparisons describe plants grown Gilroy, Calif. U.S.A. The following traits have been repeatedly observed and are determined to be basic characteristics of the new variety. The combination of these characteristics distinguishes this *Scaveola* as a new and distinct variety.

TABLE 1

DIFFERENCES BETWEEN THE NEW CULTIVAR 'BOMY WHIT' AND A SIMILAR VARIETY

| | 'Bomy Whit' | 'Scawihatis' (U.S. Plant Pat. No. 15,003) |
|---|---|---|
| Flower size | Larger | Smaller |
| Foliage color/size | Lighter/larger | Darker/smaller |
| Stem thickness | Thicker | Thinner |
| Branching | More | Fewer |

Plant:

*Form, growth and habit.*—Medium green foliage, vigorous, initially semi-upright, becoming decumbent to trailing habit with a well-branched plant habit.

*Plant height (inflorescence included).*—22–27 cm.

*Plant width.*—25–40 cm.

Foliage:

*Immature, leaf color, upper surface.*—Closest to RHS 146A.

*Lower surface.*—RHS 144A.

*Mature, leaf color, upper surface.*—Closest to RHS 146A.

*Lower surface.*—RHS 146B.

*Length.*—4.6–5.0 cm.

*Width.*—1.9–2.5 cm.

*Shape.*—Oblanceolate.

*Base shape.*—Attenuate.

*Apex shape.*—Acute.

*Margin.*—Dentate.

*Texture, upper surface.*—Somewhat pilose.

*Texture, lower surface.*—Glabrous.

*Color of veins, upper surface.*—RHS 144B basally; indistinct otherwise.

*Color of veins, lower surface.*—RHS 144B basally; indistinct otherwise.

*Petioles color.*—RHS 144B.

*Petioles length.*—0.6–0.7 cm.

*Diameter of petiole.*—0.3 cm.

*Texture.*—Slightly pilose mainly along the margins.

Stem:

*Number of main branches per plant.*—5–8.

*Number of leaves per stem.*—10–12.

*Color of stem.*—RHS 146A.

*Length of stem.*—18–21 cm.

*Diameter.*—0.3 cm.

*Length of internodes.*—0.5–2.0 cm.

*Texture.*—Slightly strigose.

*Color of peduncle.*—RHS 144B.

*Length of peduncle.*—11–20 cm.

*Peduncle diameter.*—0.3 cm.

*Texture.*—Pilose.

Inflorescence:

*Type.*—Solitary flowers arise from the leaf axils with one flower per leaf axil in an alternate arrangement but appearing so close together they appear to be cluster like. Flowers are sessile.

*Blooming habit.*—Flowers continuously from spring through the fall.

*Number of flowers per inflorescence.*—12–17 open at one time including buds.

*Duration of flowering.*—Continuous flowering throughout the Summer.

*Fragrance.*—None.

*Lastingness of individual florets.*—6–8 days.

Bud (just before opening):

*Color.*—Light RHS 1C; heavily overlaid with RHS 144C.

*Length.*—1.0–1.1 cm.

*Width.*—0.3–0.4 cm.

*Shape.*—Broadly acicular.

Corolla:

*Form.*—Composed of 5 petals fused at the base and in a semicircular or fan-like arrangement to form a lower part which is open tube-shaped; the petals are situated at obtuse angles to the flower base and do not overlap.

*Immature flower color, upper surface.*—RHS 155C but whiter along the margins; RHS 155C in the middle; RHS 144B basal blotch or 'eye' with RHS 144A striations in the blotch.

*Lower surface.*—RHS 155C along the margins, with RHS 158C in the middle.

*Mature flower color, upper surface.*—RHS 155C but whiter along the margins; RHS 155C in the middle; RHS 144B basal blotch or 'eye' with RHS 144A striations in the blotch.

*Lower surface.*—RHS 155C along the margins with RHS 158C in the middle.

*Floret diameter.*—3.3–3.6 cm.

*Floret length.*—3.1–3.2 cm.

*Petal length.*—1.6–1.7 cm.

*Petal width.*—0.4–0.5 cm.

*Petal shape.*—Oblanceolate to elliptical.

*Apex shape.*—Cuspidate.

*Margin.*—Entire.

*Petal texture, upper surface.*—Papillose.

*Lower surface.*—Glabrous.

*Corolla color, inside.*—RHS 1C; RHS 1B striations.

*Outside.*—RHS 3C with a slight RHS 1B overlay.

*Corolla length.*—1.6–1.8 cm.

*Corolla width.*—0.5–0.6 cm.

*Corolla texture, inside.*—Hirsute.

*Outside.*—Pilose.

Sepals:

*Type.*—Composed of one larger and somewhat fleshy sepal and two narrow sepals, fused at the base.

*Color of sepals.*—RHS 145A.

*Length of sepals.*—0.4–0.7 cm.

*Width of sepals.*—0.05–0.2 cm.

*Sepal shape.*—Lanceolate.

*Apex shape.*—Broadly acute.

*Margin.*—Entire.

*Texture.*—Pilose at margins on both surfaces.

Reproductive organs:

*Pistil.*—1.

*Length.*—1.2 cm.

*Stigma color.*—RHS 145B.

*Stigma texture.*—Villous.

*Stamens.*—5 protruding from the flower throat.

*Color of filaments.*—RHS N155B.

*Length of filaments.*—0.6–0.7 cm.

*Anther color.*—RHS 155C.

*Anther length.*—0.15 cm.

*Color of pollen.*—RHS 155B.

*Pollen amount.*—Sparse.

*Fertility/seed set.*—Not observed on this hybrid.

Disease/pest resistance: Disease resistance or susceptibility has not been observed on this hybrid.

What is claimed is:

1. A new and distinct variety of *Scaveola* plant named 'Bomy Whit,' substantially as illustrated and described herein.

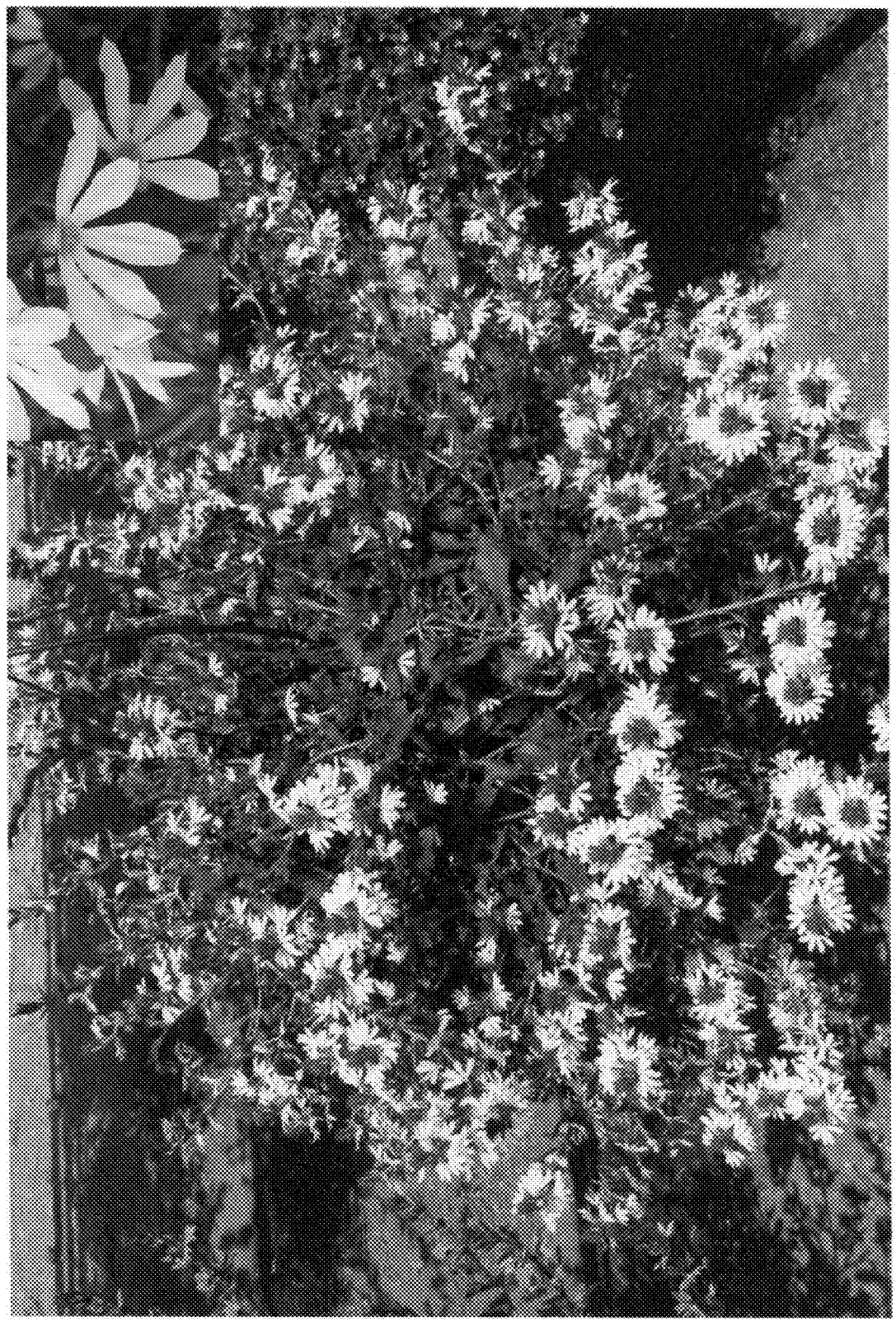

* * * * *